United States Patent
Van Der Weiden

(10) Patent No.: US 8,870,741 B2
(45) Date of Patent: Oct. 28, 2014

(54) ASSEMBLY AND METHOD FOR ATTACHING PARTICULARLY A VAGINA TO A SPINE

(75) Inventor: Robertus Mattheus Felix Van Der Weiden, Capelle Aan Den Ijssel (NL)

(73) Assignee: Karl Storz GmbH & Co. KG., Tuttlingen (DE)

( * ) Notice: Subject to any disclaimer, the term of this patent is extended or adjusted under 35 U.S.C. 154(b) by 1373 days.

(21) Appl. No.: 10/586,646

(22) PCT Filed: Jan. 19, 2005

(86) PCT No.: PCT/NL2005/000037
§ 371 (c)(1),
(2), (4) Date: Jul. 19, 2006

(87) PCT Pub. No.: WO2005/067802
PCT Pub. Date: Jul. 28, 2005

(65) Prior Publication Data
US 2008/0139878 A1    Jun. 12, 2008

Related U.S. Application Data

(60) Provisional application No. 60/537,027, filed on Jan. 20, 2004.

(30) Foreign Application Priority Data

Aug. 25, 2004    (NL) ..................... 1026909

(51) Int. Cl.
*A61F 2/00*    (2006.01)
(Continued)

(52) U.S. Cl.
CPC ......... *A61B 17/42* (2013.01); *A61B 2017/0414* (2013.01); *A61B 17/0469* (2013.01);
(Continued)

(58) Field of Classification Search
USPC ............ 600/29–32, 37; 606/1, 104, 139, 144, 606/151
See application file for complete search history.

(56) References Cited

U.S. PATENT DOCUMENTS

| 5,147,387 A | 9/1992 | Jansen |
| 5,217,486 A * | 6/1993 | Rice et al. ..................... 606/232 |

(Continued)

FOREIGN PATENT DOCUMENTS

| EP | 0 807 415 A | 11/1997 |
| EP | 1 315 467 | 6/2003 |
| WO | WO 02/19945 | 3/2002 |

OTHER PUBLICATIONS

"Colposacropexy with mesh or collagen implant and titanium bone anchors placed in sacral segments 3 and 4"; Journal of Pelvic Medicine & Surgery, vol. 9, No. 1, 9-14 (Jan./Feb. 2003; R.M.F. Van der Weiden and A.B.M. Bergkamp.
"Kortere operatie, minder klachten"; Algemeen Dagblad Oct. 3, 2003.

*Primary Examiner* — Charles A Marmor, II
*Assistant Examiner* — Carrie R Dorna
(74) *Attorney, Agent, or Firm* — Young & Thompson

(57) ABSTRACT

Assembly for attaching a patient's vaginal apex or uterus or rectum to her/his spine, includes a first tube having a length adapted to the distance from the outer wall of the patient's abdomen to the sacrum. The first tube has a distal end for engagement with the sacrum, an opposite proximal end, and a first passage from the distal to the proximal end thereof, a second tube having a length that at least equals the length of the first tube. The second tube has a distal end and an opposite proximal end, at least one attachment element with a distal end for attachment to the sacrum and a proximal end for attachment of an end of connection element for connection to the patient's vaginal apex or uterus or rectum, such as one or more threads.

24 Claims, 11 Drawing Sheets

(51) Int. Cl.
*A61B 17/42* (2006.01)
*A61B 17/04* (2006.01)
*A61B 17/34* (2006.01)
*A61B 17/00* (2006.01)

(52) U.S. Cl.
CPC ......... *A61B 17/3421* (2013.01); *A61B 17/3468* (2013.01); *A61B 17/0401* (2013.01); *A61B 2017/0409* (2013.01); *A61B 2017/00805* (2013.01); *A61B 2017/3488* (2013.01); *A61B 2017/044* (2013.01)
USPC ............................................ 600/37; 606/151

(56) References Cited

U.S. PATENT DOCUMENTS

| | | | |
|---|---|---|---|
| 5,354,292 A * | 10/1994 | Braeuer et al. | 606/1 |
| 5,458,608 A | 10/1995 | Wortrich et al. | |
| 5,954,057 A | 9/1999 | Li et al. | |
| 6,592,515 B2 | 7/2003 | Thierfelder et al. | |
| 2002/0028980 A1 | 3/2002 | Thierfelder et al. | |
| 2002/0143234 A1* | 10/2002 | LoVuolo | 600/30 |
| 2003/0078604 A1 | 4/2003 | Walshe | |
| 2003/0195386 A1 | 10/2003 | Thierfelder et al. | |
| 2004/0230092 A1 | 11/2004 | Thierfelder et al. | |

* cited by examiner

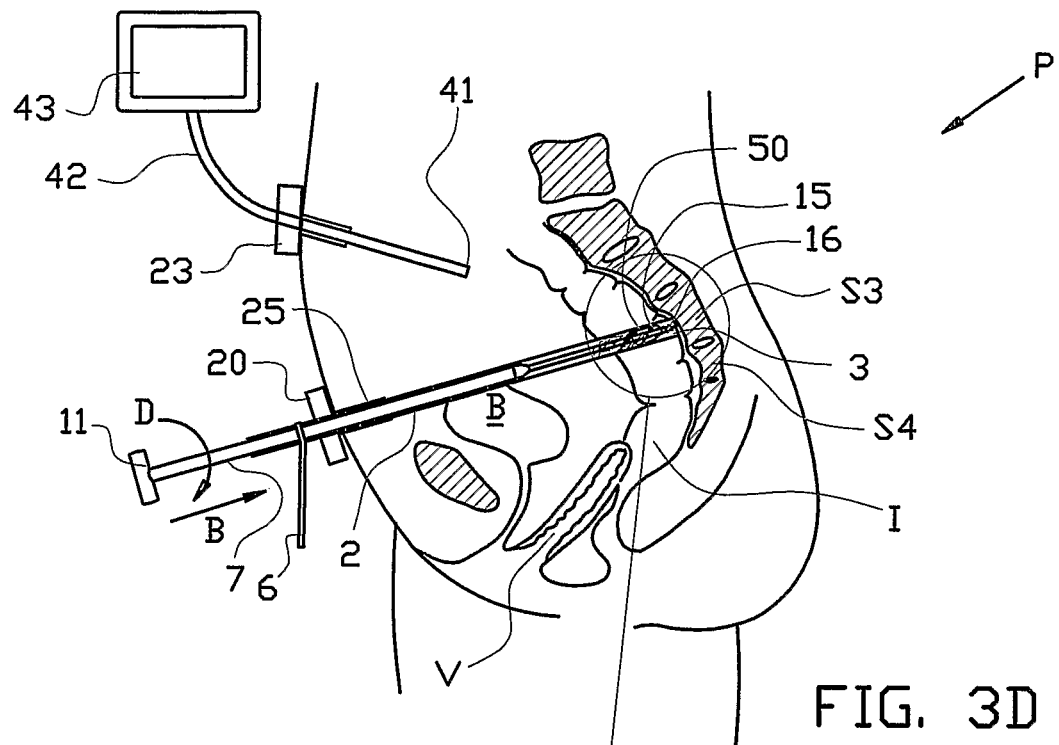
FIG. 3D
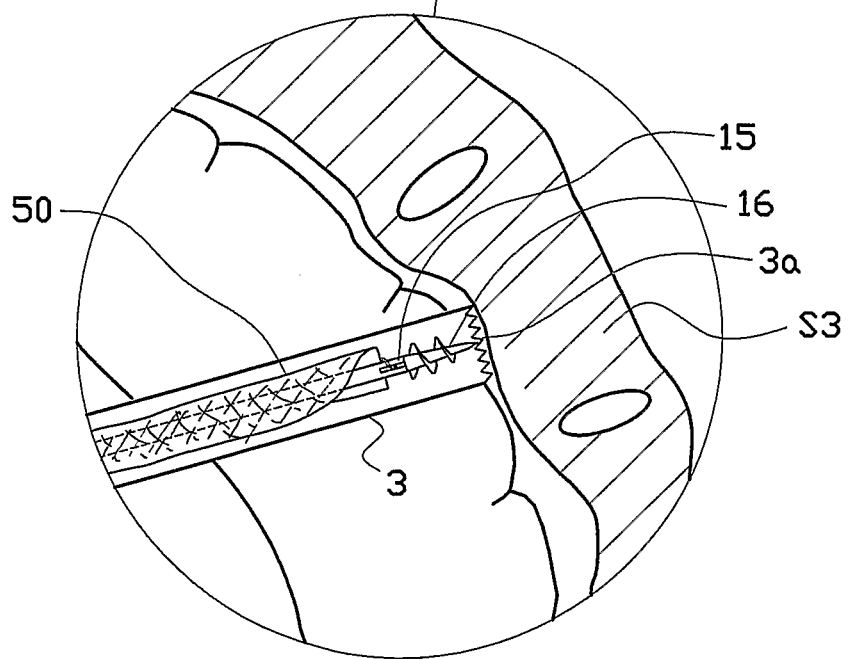

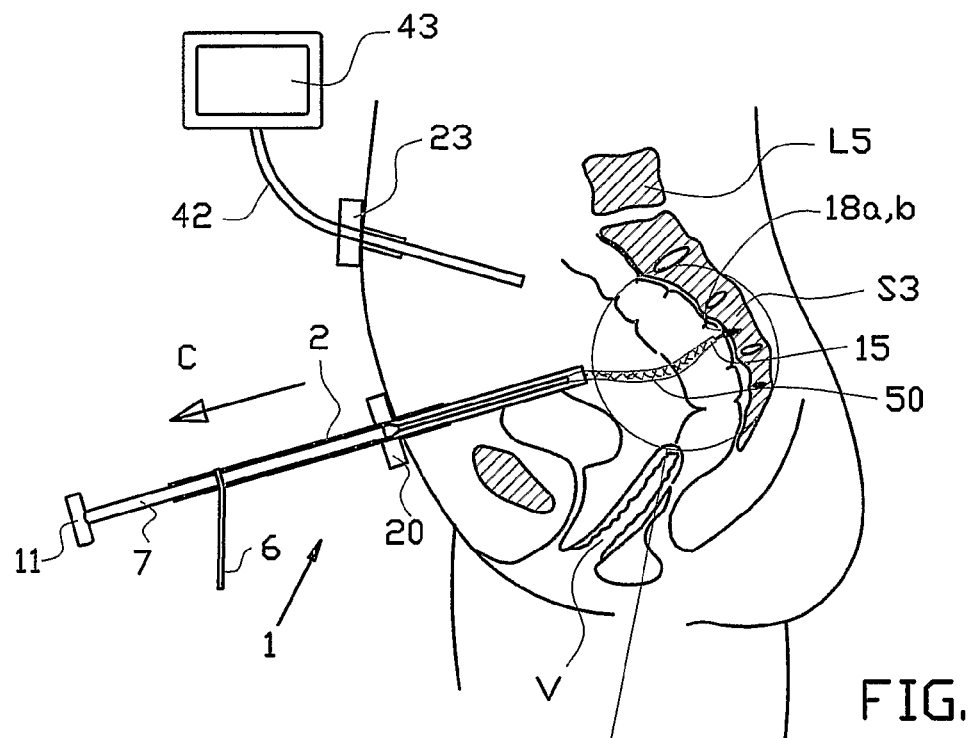
FIG. 4A
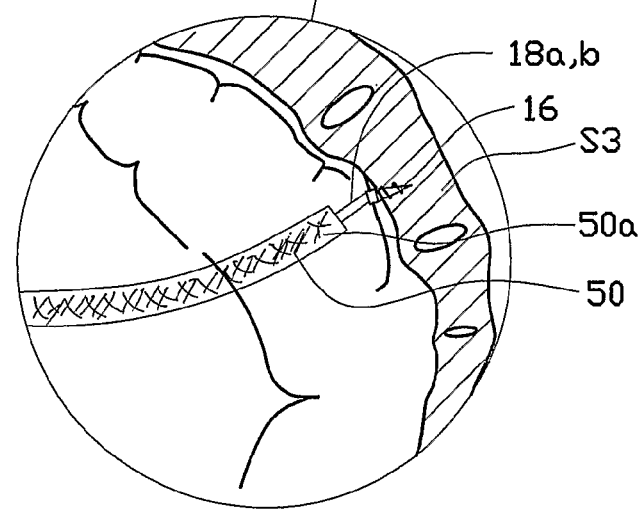

ASSEMBLY AND METHOD FOR ATTACHING PARTICULARLY A VAGINA TO A SPINE

BACKGROUND OF THE INVENTION

After a patient has had a hysterectomy, the supporting ligaments of the vagina have usually also been removed. As a consequence the vagina may bulge to the outside under pressure of other organs. A further consequence may be that the small intestine prolapses, which may cause an oppressive sensation in the lower abdomen.

In order to solve this, it is known to surgically move organs out of the way, using tools that are introduced via a large incision in the abdomen, and attach a number of threads to the upper sacral segment or further above it on one of the lumbar vertebrae, and to attach those threads to a kind of mat, that is attached to the rear side of the vagina with threads. Said mat enable tissue ingrowth of its own accord.

A drawback is that the vagina will be more upright than is the case under natural circumstances. There is also the risk of haemorrhages due to damage to blood vessels at this level of the spine, particularly the sacral promontory. An oppressive sensation in the lower abdomen might last, whereas bladder problems may also continue.

It was attempted to improve on this situation by suturing the threads at a lower location along the spine, near the coccyx. This was also done via a large incision in the abdominal wall.

After this type of surgery the patients have to stay in hospital for approximately two weeks, which entails high costs. The patients are furthermore inconvenienced by the surgery for a long time after that, particularly due to the large incision.

Similar problems may occur in case of prolapsed uteruses, particularly unpleasant oppressive sensations in the lower abdomen and/or against the bladder.

It is an object of the invention to improve on at least some of these drawbacks.

A further object of the invention is to provide an assembly and/or method wherein in case of a hysterectomy the vagina can be given a natural orientation, particularly in a quick and/or simple way.

It is a further object of the invention to provide an assembly and/or method wherein in case of a hysterectomy the vagina can be suspended to a fixed point of the patient's body in a relatively small surgical procedure.

SUMMARY OF THE INVENTION

From one aspect the invention to that end provides an assembly for use in the attachment of a patient's vaginal apex or uterus or rectum to her/his spine, comprising a first tube having a length adapted to the distance from the outer wall of the patient's abdomen to the sacrum, which first tube is provided with a distal end to be brought into engagement with the sacrum and comprising an opposite proximal end and having a first passage from the distal to the proximal end thereof, a second tube or rod having a length that at least equals the length of the first tube, which second tube or rod is provided with a distal end and comprises an opposite proximal end, at least one attachment means provided with a distal end for attachment to the sacrum and a proximal end for attachment of an end of connection means for connection to the patient's vaginal apex or uterus or rectum, such as one or more threads, wherein the distal end of the second tube or rod and the proximal end of the attachment means are formed for functional mutual engagement, wherein the second tube or rod can be movably accommodated in the first tube.

With the assembly according to the invention the connection means intended for attachment or suspension of the vagina, uterus or rectum can be attached to a lower location in the spine, due to which the orientation of the vagina or uterus etcetera, to be attached or suspended using the connections means, may correspond with the natural orientation and uncomfortable oppressive sensations can be avoided.

Preferably the second tube or rod can be snugly accommodated in the first tube. Due to the snug accommodation of the second tube or rod in the first tube the assembly can be utilised in combination with laparoscopic surgery, as a result of which the abdominal cavity need not be opened. The gas introduced into the abdominal cavity during such surgery in order to give room to intestines that have been moved out of the way by other tools, will not readily escape via both tubes. In laparoscopic surgery valves for stopping gas are otherwise used. The invention provides a valve-less assembly, which as a result is easy to manufacture and clean.

Preferably the second tube or rod can be rotatably accommodated in the first tube. The attachment means may be a bone screw or bone anchor, which screw can easily be screwed into the spine by means of the second tube or rod that is rotatable within the first tube.

For facilitating the attachment of the bone screw the proximal end of the second tube or rod may be provided with means for rotation of the second tube or rod. Ease of operation is further increased when the rotation means comprise an arm that is transverse to the second tube or rod, preferably projecting to both sides.

In one embodiment the distal end is formed for fittingly, particularly rotation-fixedly holding the proximal end of the attachment means. The second tube or rod may for instance form an internal cavity at the distal end. In said cavity the proximal end of the attachment means, particularly the bone screw, can be accommodated; preferably in a rotation-fixed manner. This is possible by using unround and/or polygonal cross-sections of hollow and proximal end of the bone screw, which cross-sections fit into each other. Thus a holding means for the attachment means is obtained in a simple way. The distal end of the second tube or rod may be narrowed.

In a further development of the assembly according to the invention, the second tube or rod extends into the first tube and at least a part of the connection means is attached to the attachment means and said part is situated within the first tube. This part of the connection means can be inserted into the abdominal cavity shielded by the first tube. Moreover the action of connection to the attachment means has taken place beforehand, so that said action need not be performed in the abdominal cavity, after placing the attachment means.

Preferably the said part of the connection means is situated between the first and the second tube or rod. Alternatively the second tube or rod may be provided with an accommodation space for them. In the first case the distal end of the second tube or rod can be narrowed for together with the first tube forming an accommodation space for said part of the connection means.

In one embodiment the distal end of the second tube or rod forms an accommodation space for the proximal end of the attachment means and it is provided with a passage to the side, wherein an end portion of the said part of the connection means, such as a thread, extends through the passage. The attachment means can thus be properly held whereas it can nonetheless already be connected to the connection means and not hinder a rotation, yet be properly reachable after placement.

At least a part of the connection means can be attached to the attachment means and be situated around the distal end of the second tube or rod, wherein said end serves as carrier for said part of the connection means.

In one practical embodiment the said part of the connection means comprises a mat of material enabling bodily tissue ingrowth.

The mat can be wrapped or shirred up around the second tube or rod in a simple way.

In one embodiment the attachment means has a diameter that at least almost corresponds to the diameter of the first passage, so that the first tube can be kept as narrow as possible to further limit the adverse effects of the surgery.

Preferably the second tube or rod at the proximal end is provided with gauge means related to the sliding of the second tube or rod in the first tube corresponding to the attachment length of the distal end of the attachment means, so that it is easy to ascertain whether the attachment means has penetrated sufficiently far into the spine.

For certainty of placement of the first tube the distal end of the first tube may be provided with a serrated edge that engages into the surface of the spine.

For enhancing the manageability of the first tube, optionally having a second tube or rod inserted therein, the first tube may be provided with a handle near the proximal end.

The connection means may comprise one or more threads that are attached to the attachment means and preferably comprise a mat of material enabling bodily tissue ingrowth, which mat can be attached to threads.

In a further development the assembly according to the invention comprises a laparoscope, and preferably a viewing screen that is functionally connected to the laparoscope.

In a further development the assembly according to the invention is sterily accommodated in a hermetically closed packaging, ready for use in surgery. The second tube or rod is then preferably inserted into the first tube.

From a further aspect the invention provides an assembly for use in the attachment of a patient's vaginal apex, uterus or rectum to her/his spine, comprising a first tube having a length adapted to the distance of the outer wall of the patient's abdomen to the sacrum, which first tube is provided with a distal end to be brought into engagement with the sacrum and comprising an opposite proximal end and having a first passage from the distal to the proximal end thereof, a second tube or rod having a length that, is at least equal to the length of the first tube, Preferably larger, which second tube or rod is provided with a distal end and comprises an opposite proximal end, at least one attachment means that is provided with means for attachment to the sacrum and means for attachment of connection means, such as one or more threads and/or a connection mat, wherein the distal end of the second tube or rod and the attachment means are formed for functional mutual engagement, wherein the first passage is suitable for accommodation of the connection means.

Preferably the first passage and the second tube or rod are adapted to each other for fitting accommodation of the second tube or rod. The connection means can be disposed between the first and the second tube or rod. The second tube or rod may form a cavity for accommodation of the connection means, particularly the said mat. The second tube or rod may form a continuous cavity, from the proximal end to the distal end.

From a further aspect the invention provides an assembly for use in surgery on a human body, comprising a first tube, provided with a distal end to be brought into engagement with a bone and comprising an opposite proximal end and having a first passage from the distal to the proximal end thereof, a second tube or rod having a length that is at least equal to the length of the first tube, preferably larger, which second tube or rod is provided with a distal end and comprises an opposite proximal end, at least one attachment means provided with means for attachment to the bone and means for attachment of connection means, such as one or more threads and/or a connection mat, wherein the distal end of the second tube or rod and the attachment means are formed for functional mutual engagement, wherein the first passage is suitable for accommodation of the connection means. Preferably the second tube forms a cavity extending from the distal end, preferably to the proximal end.

From yet a further aspect the invention provides a method for attaching the vagina to a patient's spine, wherein one or more threads are attached to the spine by means of one or more bone screws and the threads are used for indirect attachment of the vagina to the spine such as via a mat. With the bone screws and using simple tools the threads can be reliably secured to the spine remote from the spine. The incision in the abdominal wall can remain small as a result.

Preferably the bone screws are attached in the sacrum, particularly below the first segment thereof, as a result of which the orientation of the vagina after attachment to the threads can be as natural as possible.

With the threads a mat, which is known per se and which enables ingrowth of natural tissue material, can be attached to the bone screw, which mat at the other side is attached— preferably in a first step—to the vagina, particularly the rear side of the apex area of the vagina.

In one embodiment thereof an incision is made in the abdominal wall, a first tube is introduced through the incision, until it engages the spine, a bone screw is attached in the spine using a screwdriver extending through the first tube, the threads being attached to the bone screw, the first tube and the screwdriver are retracted in order to make a length of the threads attached to the bone screw free and the threads (the portions attached to the bone screw after cutting them through) are subsequently connected to the mat for attachment of the mat to the spine.

From a further aspect the invention provides a method for attaching the vagina, uterus or rectum to a patient's spine, wherein one or more connection means, particularly a mat of material enabling bodily tissue ingrowth, are introduced into the abdominal cavity and are attached to the spine by means of attachment means, after which connection means are attached to the vagina, particularly the rear side of the apex area of the vagina, uterus or rectum.

In a time-efficient embodiment the mat already attached to the attachment means is introduced into the abdominal cavity.

In one embodiment an incision is made in the abdominal wall, a first tube is introduced through the incision, until its distal end engages the spine, a bone screw is attached in the spine using a screwdriver extending through the first tube, the connection means, such as mat and/or threads, being attached to the bone screw.

The incision in the abdominal wall can be kept limited if the size of the incision is kept adjusted to a guide stub, such as a Trocar, for the insertion of the first tube. The first tube is guided by the Trocar or something similar, that may have a diameter in the order of 1 cm, so that the incision is very local.

The connection means may be inserted in a condition accommodated in the first tube.

Preferably the screwdriver used has a portion having a diameter that snugly fits the passage in the first tube, as well as a distal portion on which the mat has been arranged. If the screwdriver used has a diameter that snugly fits the passage in the first tube and is provided with a passage for the threads a leakage path between the first tube and the screwdriver is counteracted, so that possible gas in the abdominal cavity, introduced for making laparoscopic surgery possible, cannot escape to too large an extent.

For instance prior to inserting the first tube a quantity of gas may be introduced into the abdominal cavity in order to enlarge it. According to the invention after filling the abdominal cavity with gas, a laparoscope can be inserted into the abdominal cavity via an incision in the abdominal wall, which laparoscope is functionally connected to a viewing screen. The later insertion of the first tube, particularly with inserted screwdriver having the bone screw placed thereon, can be properly monitored using the laparoscope, so that the bone screw can be placed with its distal end at the wanted location on the spine.

The number of incisions can be kept limited if the laparoscope is inserted at the location where the gas has been introduced.

In a further development of the method according to the invention further incisions are made through which tools are inserted for moving the intestines and attaching the connection means, such as threads, to the vagina, uterus (preferably at the location of the ligamenta sacrouterina) or rectum. The access size also remains limited for those tools.

Preferably the screwdriver fits such into the first tube that a leakage flow of gas between them is prevented to a large extent, so that the abdominal cavity remains at sufficient gas tension.

From a further aspect the invention provides a method for attaching the vagina, uterus or rectum to a patient's spine, wherein one or more connection means, particularly connection threads are introduced into the abdominal cavity and are attached to the spine by means of attachment means, after which a mat of material enabling bodily tissue ingrowth connection means is attached to the threads and to the vagina, particularly the rear side of the apex area of the vagina, uterus or rectum.

Preferably an assembly according to the invention, as described above is used in a method according to the invention.

BRIEF DESCRIPTION OF THE DRAWINGS

The invention will be elucidated on the basis of exemplary embodiments shown in the attached drawings, in which:

FIGS. 3A-D show schematic cross-sections of the abdominal/pelvic area of a recumbent patient during the successive stages of a method according to the invention, using the assembly of the FIGS. 1A-F;

DETAILED DESCRIPTION OF THE DRAWINGS

Figure 1A:
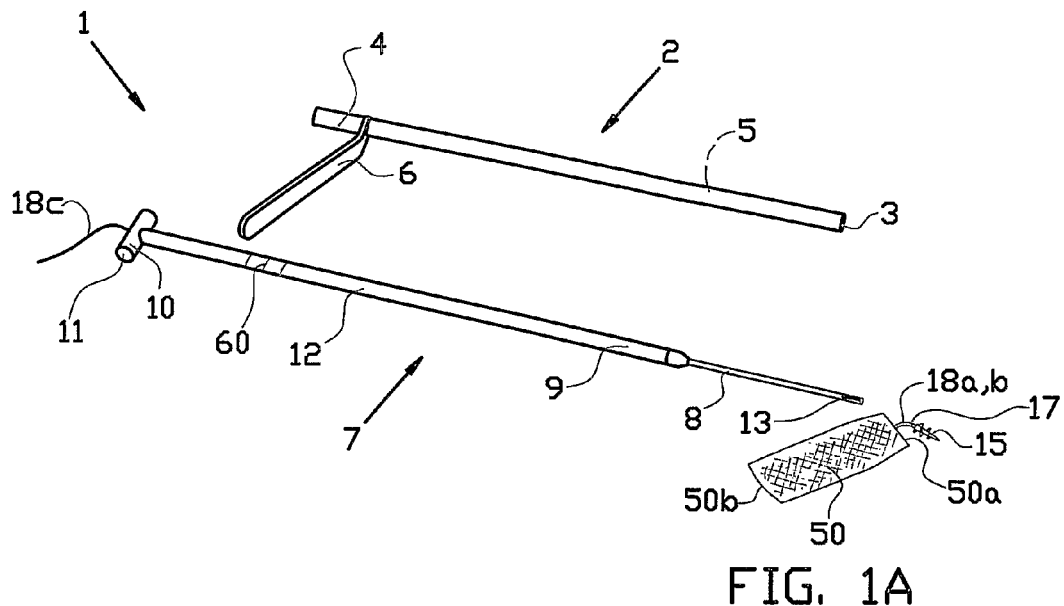
FIGS. 1A-F show a first example of a tool for an assembly according to the invention, in a first and second disassembled condition, in assembled condition and in details, respectively.
Figure 1B:
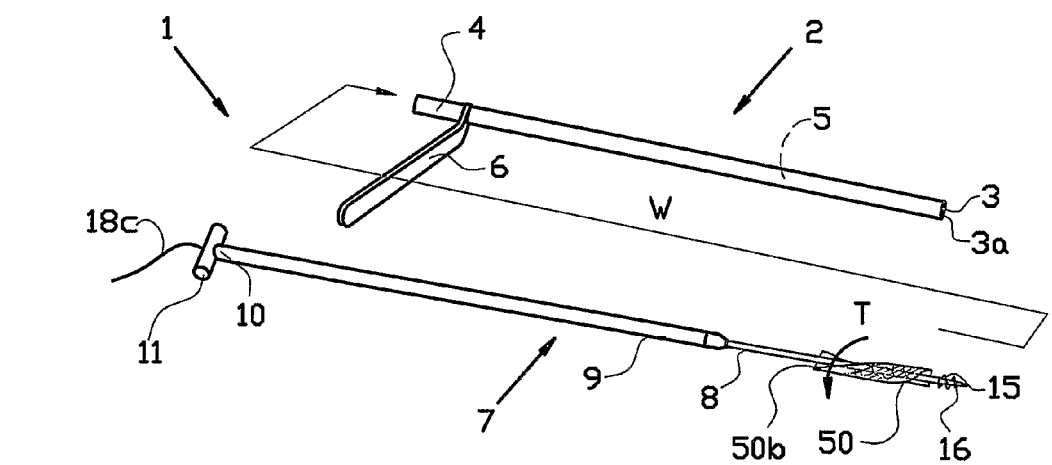
Figure 1C:
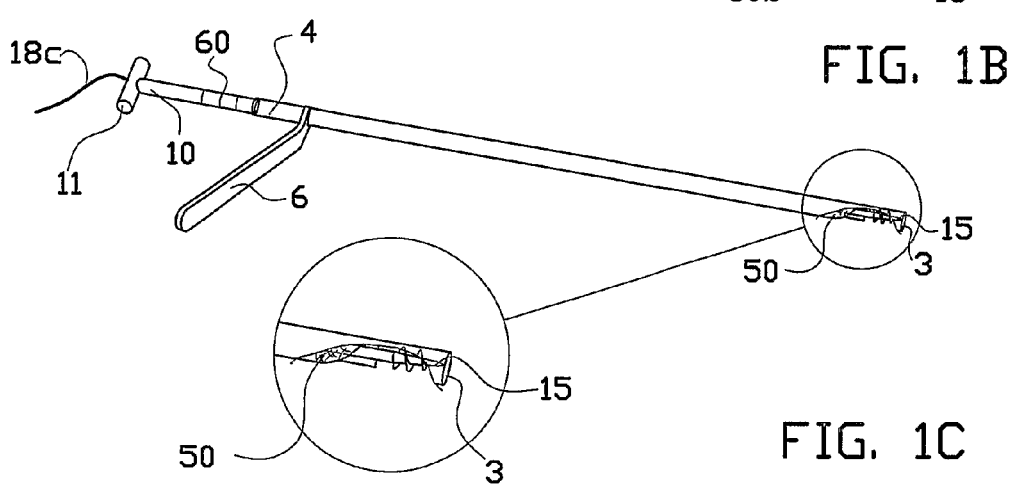

The assembly 1 in FIGS. 1A-C comprises a first, outer tube 2, made of stainless steel, having a continuous passage 5 and an open distal end 3 provided with small serrations 3a (FIG. 1F), and an open proximal end 4, near which end a handle 6 is attached to the outer tube.

The assembly 1 further comprises a second, inner tube 7, optionally having a continuous passage 12, which extends from an open, narrowed distal end portion 8, to an open proximal end 10. After approximately 8-10 cm, the distal end portion 8 changes in proximal direction into a wider portion 9, which further continues up into the proximal end 10. At the proximal end 10 a T-shaped transverse rod 11 is attached, in which the passage 12 optionally continues. At the outer surface the second tube 7 is provided with gauge marks 60, indicating a longitudinal calibration.

Figure 1D:
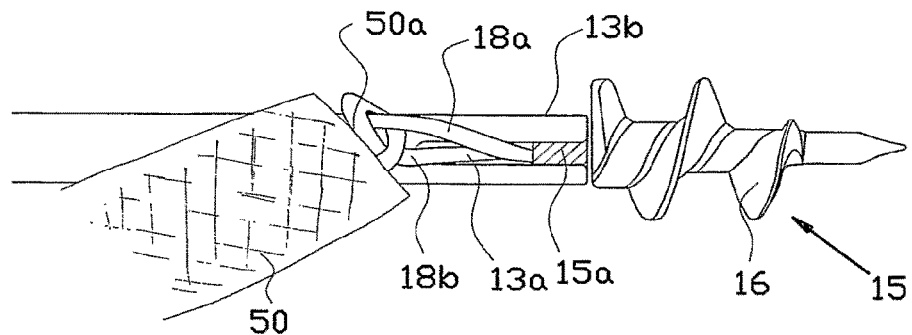
Figure 1E:
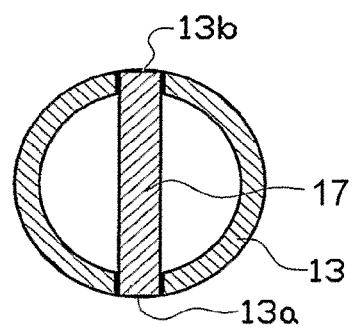
Figure 1F:
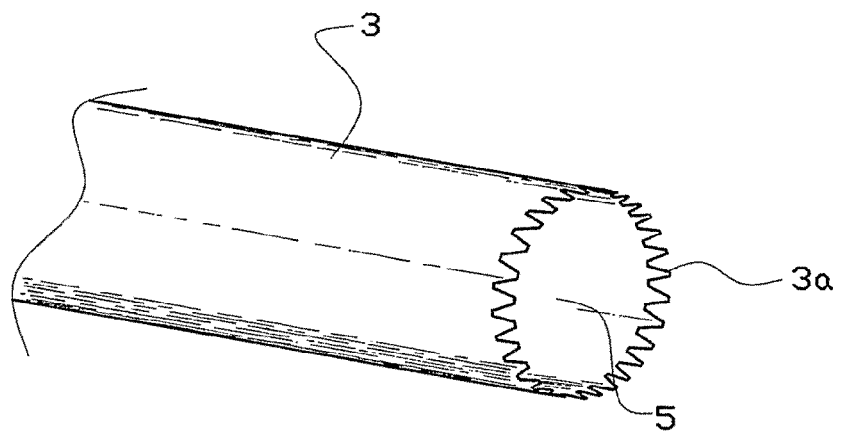

As can be seen in FIGS. 1D and 1E the distal end of the second inner tube 8 is provided with a tip 13 having two opposite slits 13a,b, forming passages from the inside to the outside.

Furthermore shown is a mat 50 forming a connection means, the mat being a rectangular piece of monofilament, knitted from polypropene gauze (Gyne mesh (soft), Ethicon, Norderstedt, Germany, having a width/length of approximately 3 cm/4 cm, which mat 50 is attached by means of threads 18a,b of a biocompatible polyester material to a titanium bone screw 15 (for instance type Arthrex AR-1925S via Arthrex (85757 Karlsfeld Germany and Naples FL34104, USA)), which is provided with a self-tapping bone screw thread 16 having a diameter of 6.5 mm and at the proximal side thereof a holder plate 17. The mat 50 can also be attached to the bone screw 15 in another way, for instance by means of a fixation ring. A screw having a wider head onto which the mat is hooked, may also be used. The holder plate 17 fits in the slits 13a,b, as can be seen in FIG. 1E, so that rotation of the tube 7 will also cause rotation of the screw 15. The holder plate 17 is furthermore held by friction in the slits 13a,b, so that the bone screw cannot inadvertently fall out of the distal end portion 8. Other ways of rotation-fixed and slip-free accommodation of the bone screw in the end portion are also possible. For instance the bone screw 15 may be provided with a hexagonal insertion pin, that clampingly fits into a distal end of the inner tube 7. If the passage 12 continues to the proximal end 10 a thread 18c may continue from the holder plate 7, and the bone screw 15 can be held in its place in the distal end portion 8 by means of a tensile force on said thread 18c.

The outer diameter of the inner tube 7 almost equals the inner diameter of the outer tube 2, so that the inner tube 7 can be slid and rotated within the outer tube 2 in a snug-fitting manner. The diameter of the bone screw 15 almost corresponds to the outer diameter of the inner tube 7. The diameter of the assembly 1 thus is as small as possible, in this example for instance 10 mm, a standard size for a Trocar which will be further discussed. The slit 13a and/or 13b is suitable for passing through the threads 18a,b, so that they need not end up in between the two tubes 2, 7. In this example the length of the outer tube 2 is 29.5 cm and the length of the inner tube 7 is 40 cm.

Figure 2A:
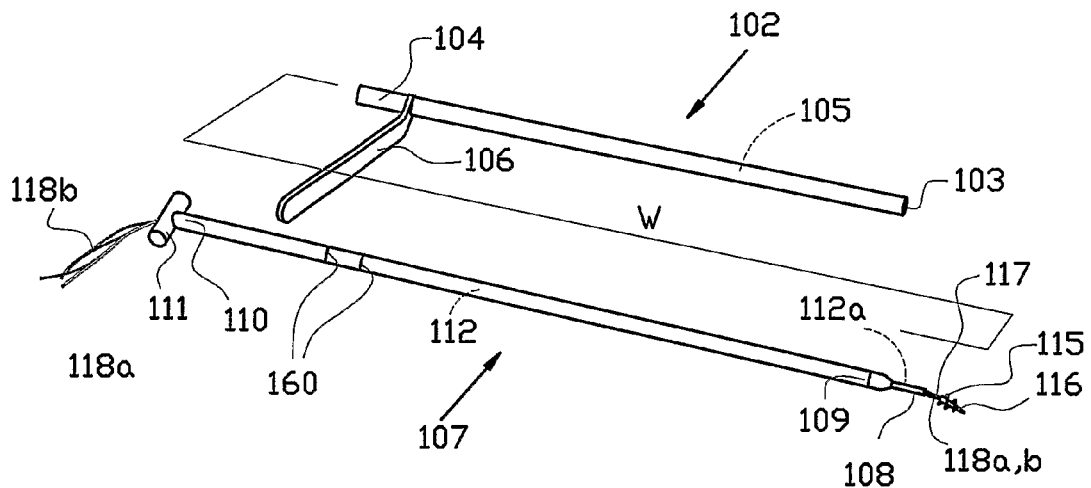
FIGS. 2A and 2B show a second example of a tool for an assembly according to the invention, in disassembled condition and assembled condition, respectively.

The assembly 101 in FIGS. 2A,B comprises a first, outer tube 102, made of stainless steel, having a continuous passage 105 and an open distal end 103 provided with small serrations 103a, and an open proximal end 104, near which end a handle 106 is attached to the outer tube 102.

The assembly 101 further comprises a second, inner tube 107, having a continuous passage 112, which extends from an open, narrowed distal end 108, to an open proximal end 10. After approximately 1 cm, the distal end 108 changes in proximal direction into a wider portion 109, which further continues up into the proximal end 110. At the proximal end 110 a T-shaped transverse rod 111 is attached, in which the passage 112 continues. The further diameters and lengths of the inner tube 107 and outer tube 102 correspond to those of the previous exemplary embodiment.

As can be seen in FIG. 2A, the connection threads 118a,b of a biocompatible polyester material have been passed from the distal end 108 to the proximal end 110, and they exit at both ends. At the distal end the threads 118a,b are attached to a bone screw 15, comparable to bone screw 15, and to a holder pin 117 situated at the proximal side thereof. The holder pin 117 is unround and fits in a rotation-fixed manner, about its centre line, in a passage portion 112a in the distal end 108, which passage portion for this purpose is correspondingly unround.

Figure 2B:
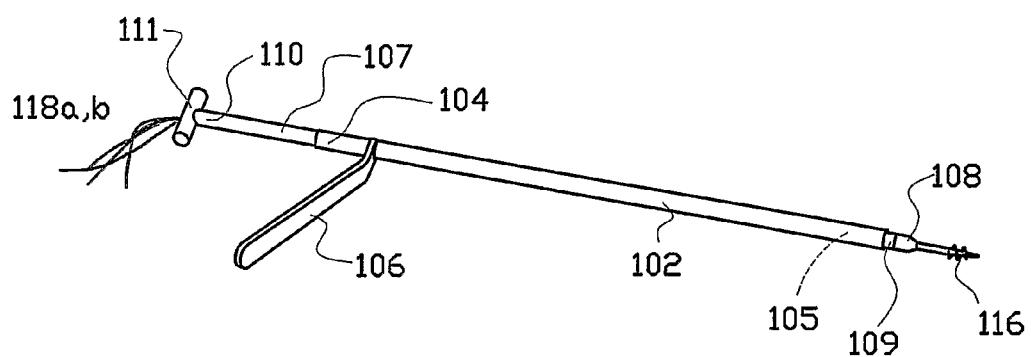

By drawing the threads 18a,b tighter at the proximal end, the pin 117 can be pulled into the passage portion 112a, and the second tube 107 is in the condition shown in FIG. 2B, in which, however, it is also accommodated in the outer tube 102. The aforementioned mat is still separate here.

Figure 3:
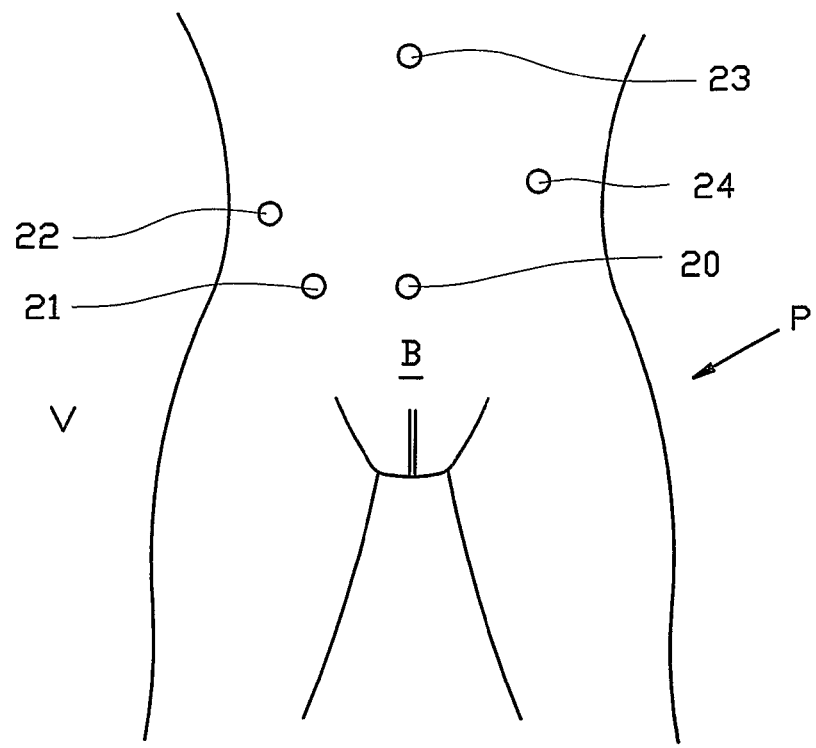
FIG. 3 shows a top view of a patient's abdomen before the treatment with an assembly according to the invention.

FIG. 3 schematically shows a surgery set-up in top view, wherein a part of patient P is shown, with abdominal wall and bladder B. Above the pubic bone a so-called Trocar placement stub 20 is placed in the median line. Similar Trocars are placed at several places in the abdominal wall at the location of 21, 22, 23 and 24. Said Trocars are standard auxiliary tools in laparoscopic surgery, and are placed after making a small local incision in the abdominal wall, and with a narrowed portion extend through the abdominal wall, and are provided with continuous passages, as well as with a sealing therein, which sealing allows a tool through in a slidable, sealing manner.

Figure 3A:
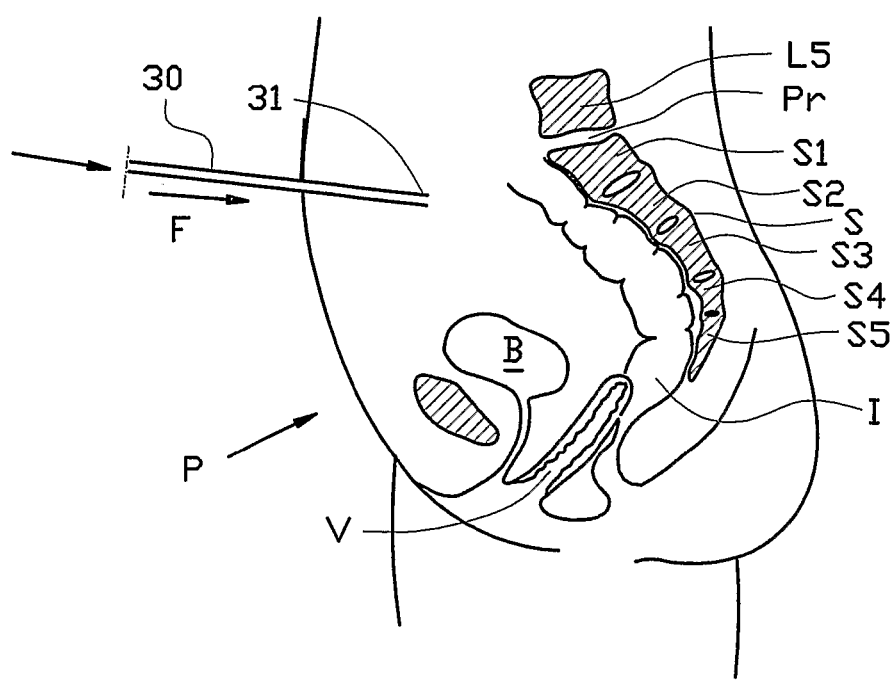

FIG. 3A shows the sacral segments S1-S5, as well as the fifth lumbar vertebra L5 and the transition therebetween, sacral promontory Pr.

Prior to placing the Trocars 20-24 a small incision is made at the location of (later on) wanted location of Trocar 23 and an insufflation needle 30, provided with a distal end 31 is inserted (direction F) through the abdominal wall into the abdominal cavity, after which carbon dioxide is introduced into the abdominal cavity (FIG. 3A) via the tube 30. As a result the volume of the abdominal cavity B is enlarged, due to which room is provided for engaging and moving the vagina V and the intestines I during the subsequent actions and surgery.

Subsequently the insufflation needle 30 is retracted, and— after making the incision larger—the Trocar 23 is inserted. Due to the enlargement of the abdominal cavity this can take place safely. Gas escaping from the abdominal cavity is counteracted by the sealings in the Trocar 23.

Figure 3B:
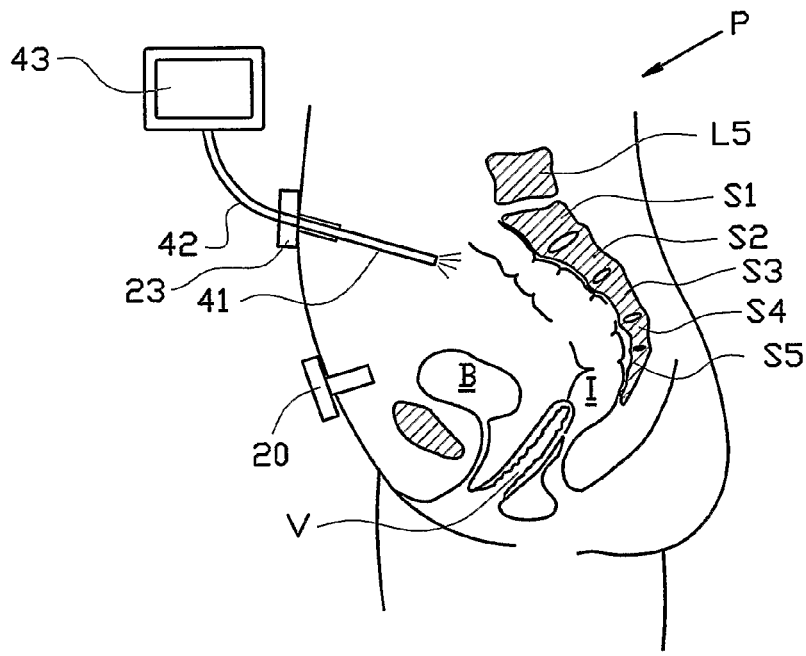

Trocar 23, as shown in FIG. 3B, is used for inserting a laparoscope 40 into the abdominal cavity, which laparoscope is provided with a view end 41 and which by means of line 42 is functionally connected to monitor 43. Via the monitor 43, the abdominal cavity can be viewed using the end 41 of the laparoscope 40.

While being monitored by the laparoscope, the other Trocars 20, 21, 24 and 25 are inserted. They also provided with sealings for counteracting the escape of gas from the abdominal cavity.

Then the tools can be inserted in a controlled manner via the Trocars 21, 23 and 24.

Figure 3C:
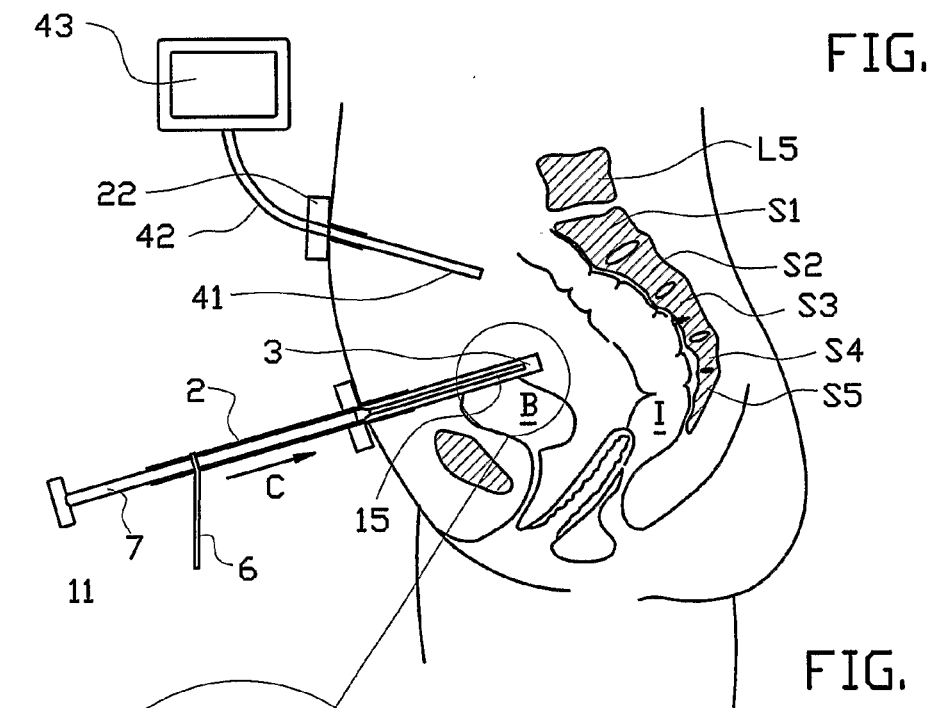
Figure 3C:
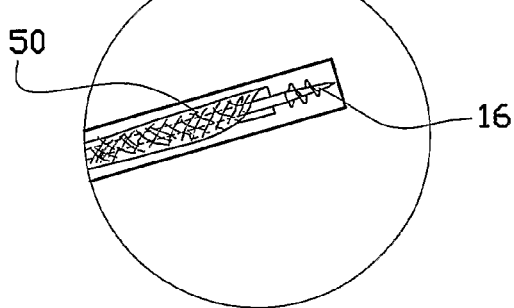

Monitored via the laparoscope 40, the assembly of FIG. 1C is inserted via the Trocar 20, as shown in FIG. 3C. Due to the snug fit of the inner tube 2 in the outer tube 7 hardly any gas will be able to escape from the abdominal cavity.

The insertion of the assembly 1, monitored by means of the laparoscope 40, takes place such that the distal end 3 with the serrations 3a abuts an area of the spine that is situated relatively low, in this example the third segment S3 of the sacrum. When inserting the assembly 1 the bladder B and the bowels I are kept pushed aside by tools, so that the placement can take place correctly.

When the serrations 3a of the distal end 3 are in proper engagement with the sacral segment S3, the bone screw 15 is pressed against the sacral segment S3 or S4 in the median line, by pressing the proximal end 10 of the inner tube 7. Subsequently by engaging the T-part 11 with the fingers, the inner tube 7 is rotated about its axis within the outer tube 2, as a result of which the bone screw 15 with treaded part 16 is screwed into the sacral segment S3 (FIG. 3D).

When based on movement/position of the grade marks 60 with respect to the proximal edge of the first tube 2 it is ascertained that the inner tube 7 has moved a distance in distal direction in the tube 2, which distance corresponds to the length of the screw thread 16, the surgeon will stop rotating the T-transverse piece 11. Subsequently he will first retract the inner tube 7 a few centimeters in order to release the bone screw 15 from the distal end 8. Subsequently the assembly 1, optionally first the first tube 2 separately over some distance, is retracted, leaving behind the mat 50 that is connected to the bone screw 15 by means of threads 18a,b (FIG. 4A).

Figure 4B:
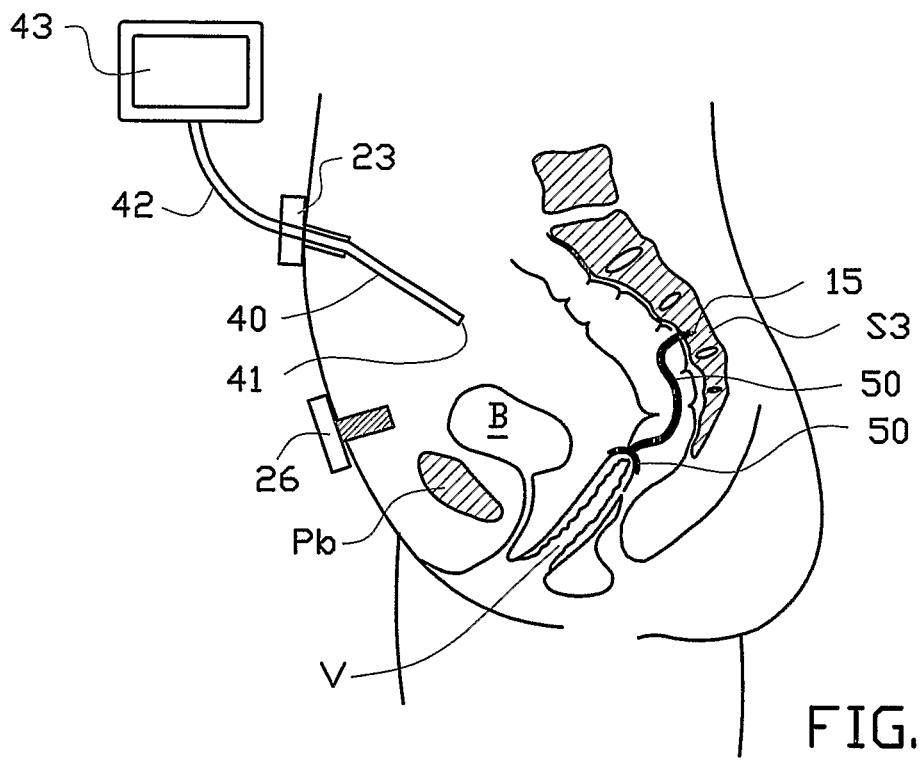
FIGS. 4A,B show two next stages in a method according to the invention, following FIG. 3D in a recumbent patient.
FIG. 4C shows the result of the method according to the invention.

The free end of the mat 50 is subsequently engaged by tools inserted through the Trocars, and using further tools inserted through the Trocars, is attached with sutures near one of the mat edges to the rear side of the vaginal apex, particularly the posterior vaginal wall, using four mersilene or ethibond sutures (Ethicon, Norderstedt, Germany) (FIG. 4B).

Figure 4C:
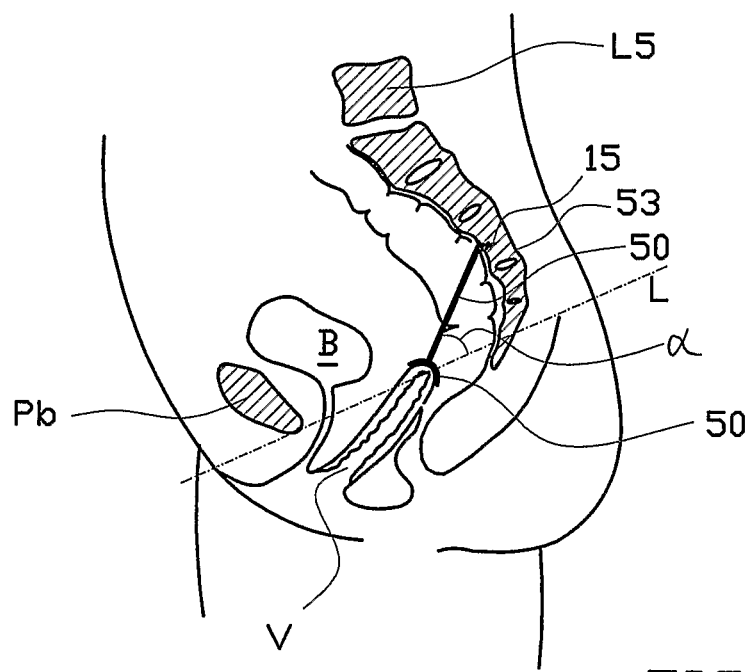

The mat 50—in the recumbent position of the patient— extends tensionless between the vagina and the bone screw 15 (and thus S3 or S4). The vaginal axis is in an anatomically correct position (FIG. 4C).

After it is ascertained by means of the laparoscope 40 that the attachment of the vagina has been realised as desired, the tools are retracted from the abdominal cavity and from the Trocars, and the Trocars are removed and the incisions are sutured.

In the upright position of the patient (FIG. 4C) the mat 50, connecting the vaginal apex with S3 or S4, ensures that the vagina will not sag. In FIG. 4C it can also be seen that the vagina has assumed a more natural orientation. Line L is drawn as a reference thereof, which line connects the lower edge of the pubic bone (Pb) with the lower side of S5 in the sagittal plane (the pubococcygeal reference line). The angle α the mat 50 is at to the line L preferably is less than 45°.

It is noted that the bone screw 15 may alternatively be placed in S2. Under certain conditions S5 can also be used.

When carrying out the method according to the invention on a uterus the mat 50 is sutured to the uterus at the location of the attachment of the ligamenta sacrouterina. In this embodiment the mat itself has also been attached to the bone screw beforehand by means of threads or other connection means.

When using the assembly 101 of the FIGS. 2A,B the sequence may be slightly different. After the actions that are part of FIGS. 3A,B have been carried out, the mat 50 that has not yet been attached to the bone screw 115 is, while being monitored by the laparoscope 40, first inserted and by means of tools inserted through the Trocars, with sutures near one of the mat edges attached to the rear side of the vaginal apex, particularly the posterior vaginal wall, using four mersilene or ethibond sutures (Ethicon, Norderstedt, Germany). It is noted that for the sake of clarity the mat 50 has been left out in the FIGS. 5A,B and 6A.

Figure 5A:
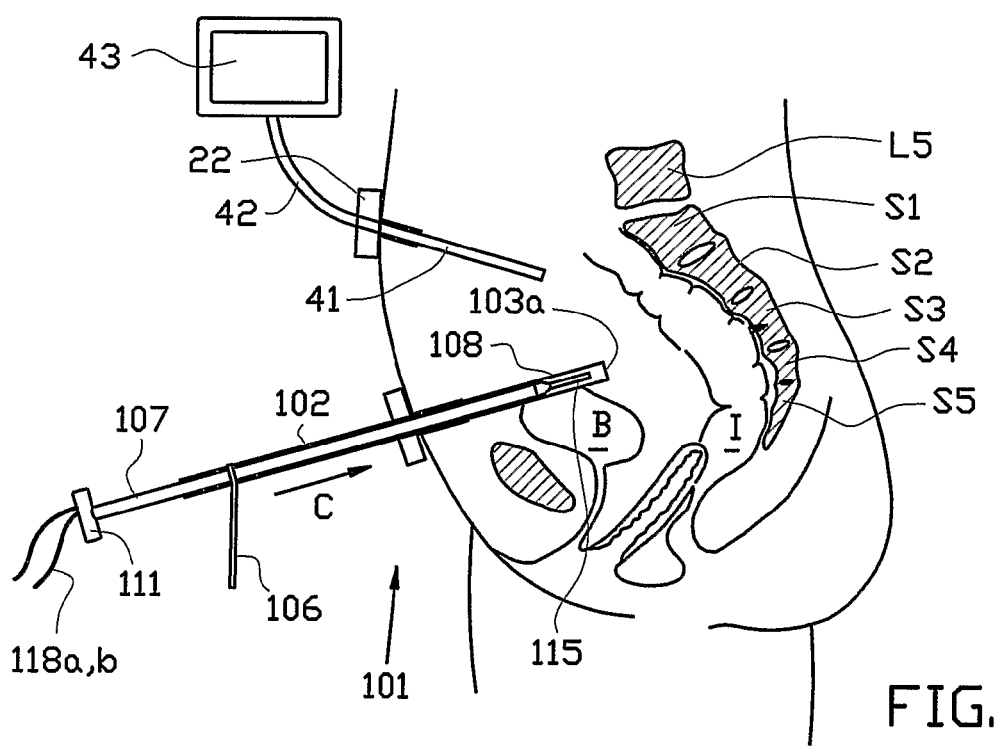
FIGS. 5A,B show schematic cross-sections of the abdominal/pelvic area of a recumbent patient during consecutive stages of a method according to the invention using the assembly of the FIGS. 2A,B.

Via the Trocar 20 the assembly 101 of FIG. 2B is inserted, as shown in FIG. 5A. Due to the snug fit of the inner tube 102 in the outer tube 107 hardly any gas will be able to escape from the abdominal cavity.

The insertion of the assembly 101, monitored by means the laparoscope 40, takes place such that the distal end 103 with the serrations 103a abuts an area of the spine that is situated relatively low, in this example the third segment S3 of the sacrum. When inserting the assembly 1 the bladder B and the bowels I are kept pushed aside by tools, so that placement can take place correctly. By pulling the thread 118a,b extending out of the proximal end 110, the bone screw 115 can be pulled in place in end 103.

Figure 5B:
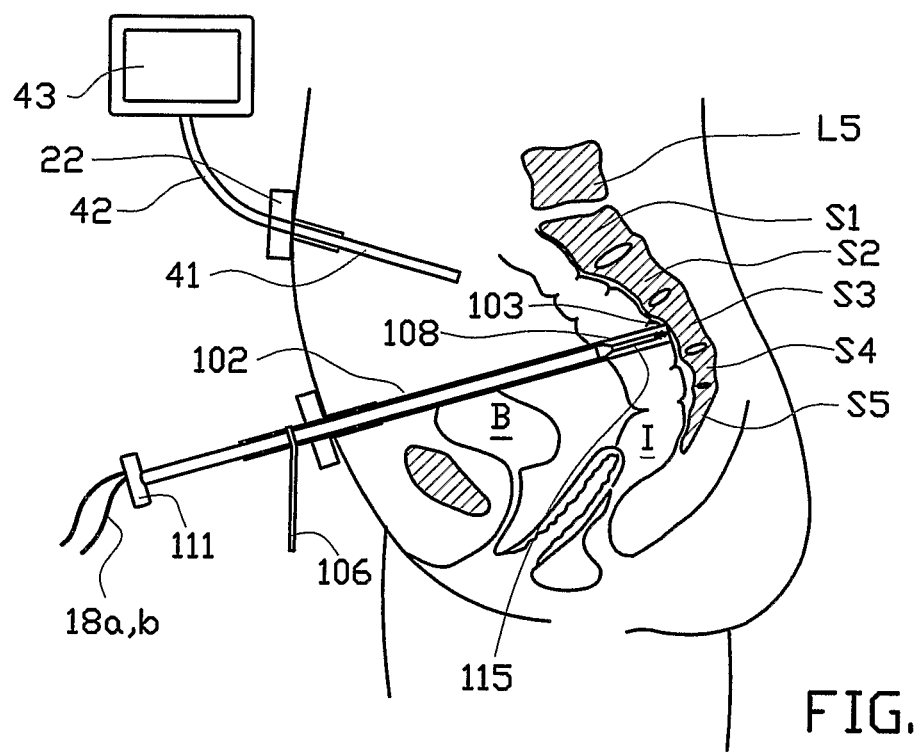

When the serrations 103a of the distal end 103 are in proper engagement with sacral segment. S3, the bone screw 115 is pressed against the sacral segment S3 or S4 in the median line, by pressing the proximal end 110 of the inner tube 107. Subsequently by engaging T-part 111 with the fingers, the inner tube 107 is rotated about its axis within the outer tube 102, as a result of which the bone screw 115 with threaded part 116 is screwed into the sacral segment S3 (FIG. 5B).

Figure 6A:
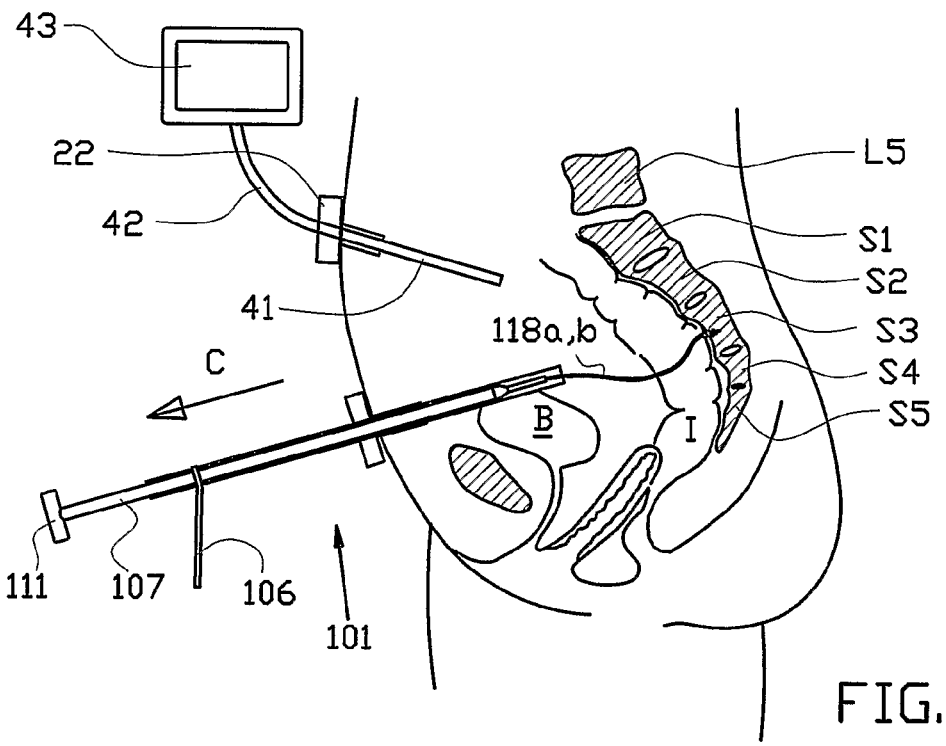
FIGS. 6A,B show two next stages in a method according to the invention, following FIG. 5B in a recumbent patient.

When based on movement of the grade marks 60 it is ascertained that the inner tube 107 has moved a distance in distal direction in the tube 102, which distance corresponds to the length of the screw thread 116, the surgeon will stop rotating the T-transverse piece 111. Subsequently he will first retract the inner tube 107 a few centimeters in order to release the bone screw 115 from the distal end 108. Subsequently the assembly 101 is retracted from the abdominal cavity B, wherein the threads 118a,b that are connected to the bone screw 115, particularly its pin 117, slide through the passages 112, 112a and exit from the distal end 108 of the inner tube 107 (FIG. 6A). The threads 118a,b are then cut off at approximately 10 cm from the bone screw 115.

Figure 6B:
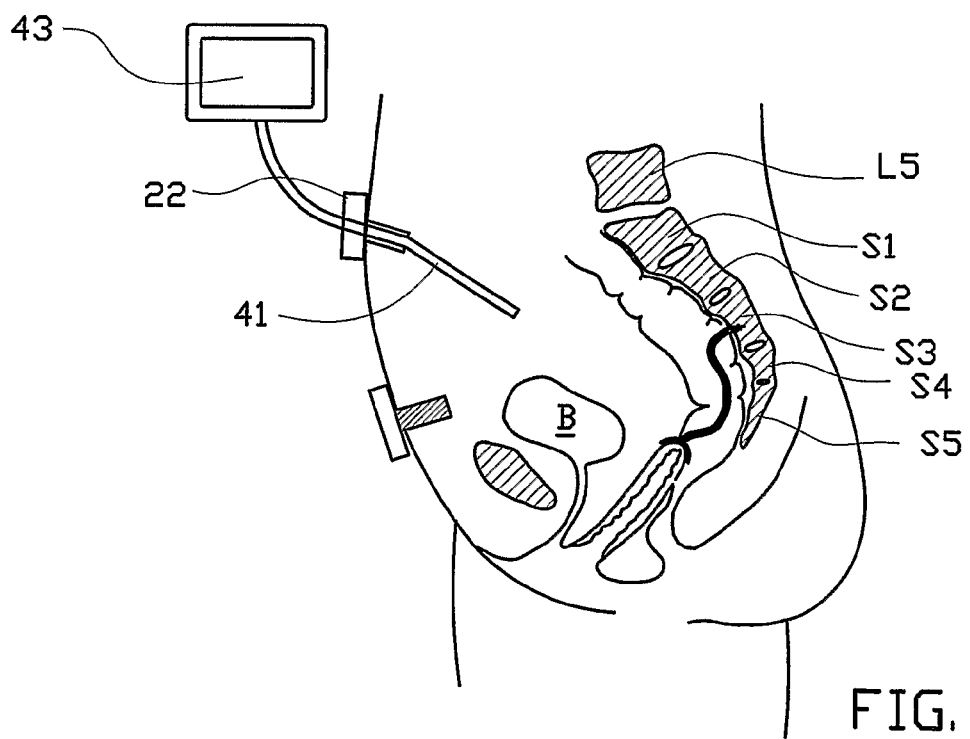

This released portion of the threads 118a,b can then be engaged by means of tools from the other Trocars. The threads 118a,b are passed through the mat near the free opposite mat edge and subsequently the mat 50 is placed at the lowest point of the abdominal cavity B (the cavum Douglasi). The threads 118a,b passed through the mat 50 are drawn tighter as a result of which the mat edge 50a is pulled towards the bone screw (FIG. 6B). Subsequently the threads 118a,b are tied, and the situation as shown in FIG. 4C is achieved.

The method and the assembly according to the invention can also be used for fixation of the rectum.

The invention claimed is:

1. An assembly for use in the attachment of a patient's vaginal apex or uterus or rectum to her/his spine, comprising:
a first tube having a length adapted to a distance from an outer wall of the patient's abdomen to a sacrum, the first tube being provided with a distal end and comprising an opposite proximal end and having a first passage from the distal to the proximal end thereof;
a second tube or rod having a length that at least equals the length of the first tube, the second tube or rod being provided with a distal end and comprises an opposite proximal end;
a connector for connection to the patient's vaginal apex or uterus or rectum;
at least one attachment device configured for penetrating into the spine provided with a distal end for attachment to the sacrum and a proximal end for attachment of an end of said connector wherein the distal end of the second tube or rod and the proximal end of the attachment device are formed for functional mutual engagement; and
at least one thread connected at a first end to the proximal end of the attachment device and at a second end to the connector for attaching the attachment device to the connector,
wherein the second tube or rod can be movably accommodated in the first tube, the second tube or rod extending into the first tube,
the distal end of the first tube is configured to be brought into engagement with the sacrum and at least a part of the connector is attached to the attachment device and situated within the first tube,
the part of the connector is situated between the first and the second tube or rod, the connector being completely positioned within the first tube, and
a distal end portion of the second tube or rod is narrowed for together with the first tube forming an accommodation space for said part of the connector.

2. The assembly according to claim 1, wherein the second tube or rod can be rotatably accommodated in the first tube.

3. The assembly according to claim 2, wherein the attachment device is a bone screw.

4. The assembly according to claim 2, wherein the proximal end of the second tube or rod is provided with means for rotation of the second tube or rod.

5. The assembly according to claim 4, wherein the means for rotation comprises an arm that is transverse to the second tube or rod.

6. The assembly according to claim 1, wherein the distal end of the second tube or rod is formed for fittingly, holding the proximal end of the attachment device.

7. The assembly according to claim 6, wherein the second tube or rod has an internal cavity, which is at least formed at the distal end.

8. The assembly according to claim 1, wherein the second tube or rod has an internal cavity, which is at least formed at the distal end, and wherein the distal end of the second tube or rod forms an accommodation space for the proximal end of the attachment device and is provided with a passage to the side, wherein an end portion of the said part of the connector extends through the passage.

9. The assembly according to claim 1, wherein the said part of the connector comprises a mat of material enabling bodily tissue ingrowth.

10. The assembly according to claim 9, wherein the mat is wrapped or shirred up around the second tube or rod.

11. The assembly according to claim 1, wherein the attachment device has a diameter that at least almost corresponds to the diameter of the first passage.

12. The assembly according to claim 1, wherein the second tube or rod at the proximal end is provided with means for gauging related to the sliding of the second tube or rod in the first tube corresponding to an attachment length of the distal end of the attachment device.

13. The assembly according to claim 1, wherein the distal end of the first tube is provided with a serrated edge.

14. The assembly according to claim 1, wherein the first tube is provided with a handle near the proximal end.

15. The assembly according to claim 1, wherein the connector comprises:
a mat of material enabling bodily tissue ingrowth.

16. The assembly according to claim 15, wherein the mat of material is attached to threads.

17. The assembly according to claim 1, further comprising a laparoscope.

18. The assembly according to claim 17, further comprising a viewing screen that is functionally connected to the laparoscope.

19. The assembly according to claim 1, sterilely accommodated in a hermetically closed packaging.

20. The assembly according to claim 1, wherein the second tube or rod is snugly accommodated in the first tube.

21. The assembly according to claim 1, wherein the assembly is configured to be movably inserted in an abdominal cavity via a trocar.

22. The assembly according to claim 1, wherein said narrowed distal end portion of the second tube or rod is provided with slits for passing through said at least one thread, such that, during use, said at least one thread does not end up in between the first and second tube.

23. A device for the attachment of a patient's vaginal apex or uterus or rectum to her/his spine, comprising:
a trocar; and
an assembly comprising:
a first tube having a length adapted to a distance from an outer wall of the patient's abdomen to a sacrum, the first tube being provided with a distal end and comprising an opposite proximal end and having a first passage from the distal to the proximal end thereof;
a second tube or rod having a length that at least equals the length of the first tube, the second tube or rod being provided with a distal end and comprises an opposite proximal end;
a connector for connection to the patient's vaginal apex or uterus or rectum;
at least one attachment device configured for penetrating into the spine provided with a distal end for attachment to the sacrum and a proximal end for attachment of an end of said connector wherein the distal end of the second tube or rod and the proximal end of the attachment device are formed for functional mutual engagement; and
at least one thread connected at a first end to the proximal end of the attachment device and at a second end to the connector for attaching the attachment device to the connector,
wherein the second tube or rod can be movably accommodated in the first tube, the second tube or rod extending into the first tube,
the distal end of the first tube is configured to be brought into engagement with the sacrum and at least a part of the connector is attached to the attachment device and the connector is completely positioned within the first tube,
the part of the connector is situated between the first and the second tube or rod,
a distal end portion of the second tube or rod is narrowed for together with the first tube forming an accommodation space for said part of the connector, and
the assembly is configured to be movably inserted in an abdominal cavity via the trocar.

24. The device according to claim 23, wherein said narrowed distal end portion of the second tube or rod is provided with slits for passing through said at least one thread, such that, during use, said at least one thread does not end up in between the first and second tube.

* * * * *